(12) United States Patent
Butler et al.

(10) Patent No.: US 8,721,689 B2
(45) Date of Patent: May 13, 2014

(54) MULTI-AXIAL SPINAL CROSS-CONNECTORS

(75) Inventors: Michael S. Butler, St. Charles, IL (US); Michael J. Milella, Jr., Schaumburg, IL (US); Kara A. Bucci, Palos Park, IL (US)

(73) Assignee: Life Spine, Inc., Hoffman Estates, IL (US)

( * ) Notice: Subject to any disclaimer, the term of this patent is extended or adjusted under 35 U.S.C. 154(b) by 1709 days.

(21) Appl. No.: 11/906,804

(22) Filed: Oct. 4, 2007

(65) Prior Publication Data

US 2008/0086134 A1 Apr. 10, 2008

Related U.S. Application Data

(60) Provisional application No. 60/849,230, filed on Oct. 4, 2006.

(51) Int. Cl.
*A61B 17/70* (2006.01)
(52) U.S. Cl.
USPC .............................. 606/252; 606/253; 606/278
(58) Field of Classification Search
CPC .... A61B 17/68; A61B 17/70; A61B 17/7004; A61B 17/7019; A61B 17/7043; A61B 17/7049; A61B 17/705; A61B 17/7052; A61B 2017/7073
USPC ................... 606/246, 250–253, 278, 279, 64; 403/373, 389, 52, 55, 63, 72–74, 87, 403/303, 337, 374.3, 385, 391, 396, 399
See application file for complete search history.

(56) References Cited

U.S. PATENT DOCUMENTS

| | | | | |
|---|---|---|---|---|
| 5,020,195 A | * | 6/1991 | LeVahn | 24/514 |
| 5,667,526 A | | 9/1997 | Levin | |
| 5,727,899 A | * | 3/1998 | Dobrovolny | 403/389 |
| 5,792,046 A | * | 8/1998 | Dobrovolny | 600/234 |
| 5,947,966 A | | 9/1999 | Drewry et al. | |
| 6,017,306 A | * | 1/2000 | Bigliani et al. | 600/234 |
| 6,096,039 A | | 8/2000 | Stoltenberg et al. | |
| 6,110,173 A | | 8/2000 | Thomas, Jr. | |
| 6,123,482 A | * | 9/2000 | Keller | 403/384 |
| 6,238,396 B1 | | 5/2001 | Lombardo | |
| 6,311,586 B1 | | 11/2001 | Hirse | |
| 6,524,310 B1 | * | 2/2003 | Lombardo et al. | 606/250 |

(Continued)

OTHER PUBLICATIONS

Written Opinion of the International Search Authority for PCT Application No. PCT/US2008/069899, mailing date Sep. 8, 2008, 4 pages.

*Primary Examiner* — Pedro Philogene
*Assistant Examiner* — Lynnsy Schneider
(74) *Attorney, Agent, or Firm* — Foley & Lardner LLP

(57) ABSTRACT

A multi-axial spinal cross-connector is configured for connection between spinal fixation devices such as spinal fixation rods. The cross-connector has first and second connection members that are joinable at a fixable pivot junction. The pivot junction allows the connection members to assume various positions relative to one another. A clamp is provided on each end of the first and second connection members whose open and closed states are controlled by fixation of a pivot structure which also fixates the positions of the first and second connection members relative to each other. The cross-connector provides single and/or multi-step locking of both end clamps at the pivot joint. The cross-connector also provides easy in situ sizing, positioning and adjustability.

20 Claims, 15 Drawing Sheets

(56) References Cited

U.S. PATENT DOCUMENTS

| | | | |
|---|---|---|---|
| 6,616,664 B2 * | 9/2003 | Walulik et al. | 606/57 |
| 6,736,775 B2 * | 5/2004 | Phillips | 600/234 |
| 7,314,331 B1 * | 1/2008 | Koros et al. | 403/396 |
| 7,553,279 B1 * | 6/2009 | Phillips et al. | 600/234 |
| 7,666,210 B2 | 2/2010 | Franck et al. | |
| 7,744,632 B2 | 6/2010 | Usher | |
| 7,749,163 B2 * | 7/2010 | Mulac et al. | 600/234 |
| 7,806,623 B2 * | 10/2010 | Thomke et al. | 403/385 |
| 2003/0114853 A1 * | 6/2003 | Burgess et al. | 606/61 |
| 2005/0113831 A1 * | 5/2005 | Franck et al. | 606/61 |
| 2005/0228377 A1 | 10/2005 | Chao et al. | |
| 2006/0064093 A1 | 3/2006 | Thramann et al. | |
| 2006/0206114 A1 * | 9/2006 | Ensign et al. | 606/61 |
| 2006/0271045 A1 | 11/2006 | Hubbard et al. | |
| 2007/0049932 A1 * | 3/2007 | Richelsoph et al. | 606/61 |
| 2007/0233090 A1 | 10/2007 | Naifeh et al. | |
| 2009/0228046 A1 | 9/2009 | Garamszegi | |

* cited by examiner

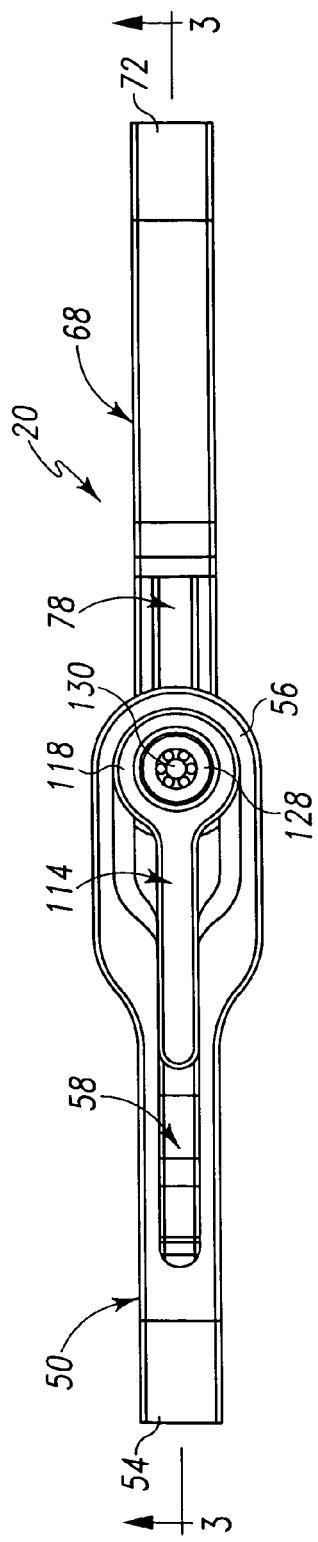
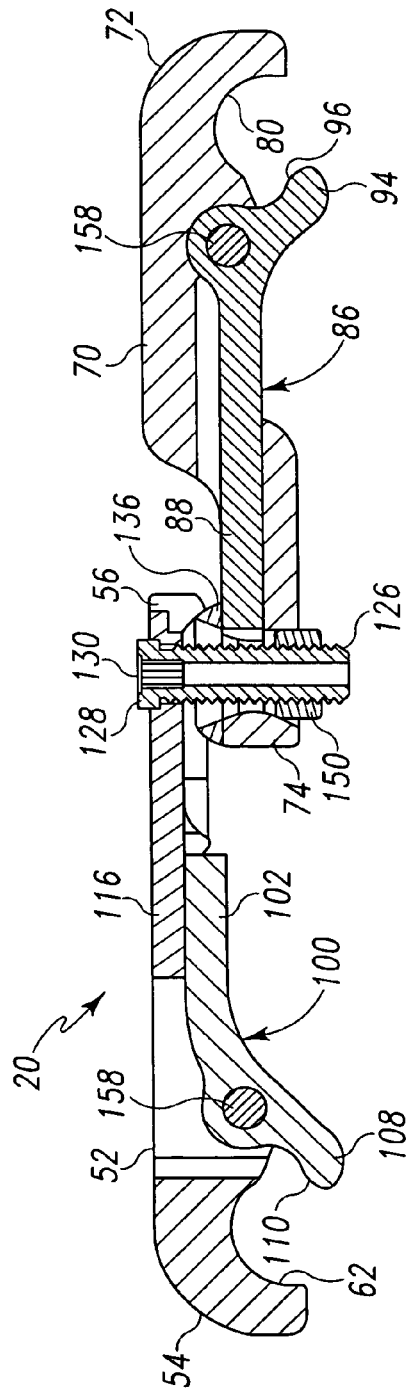
Fig. 2
Fig. 3

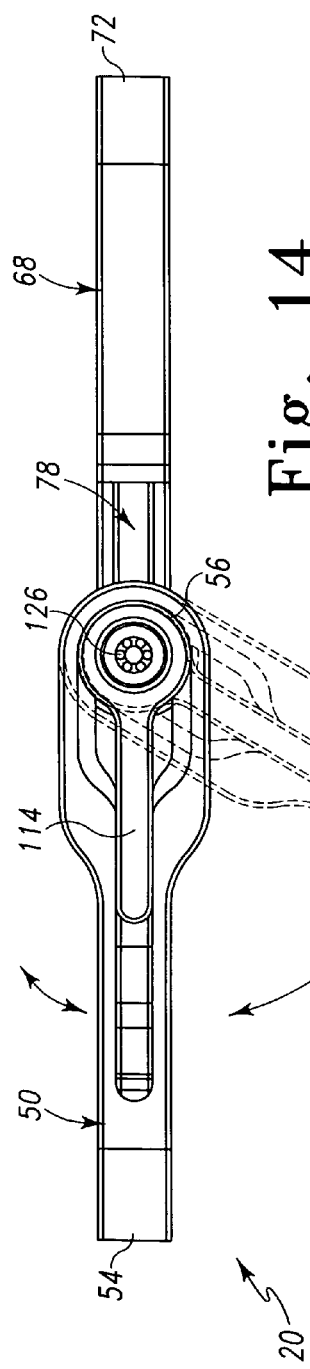
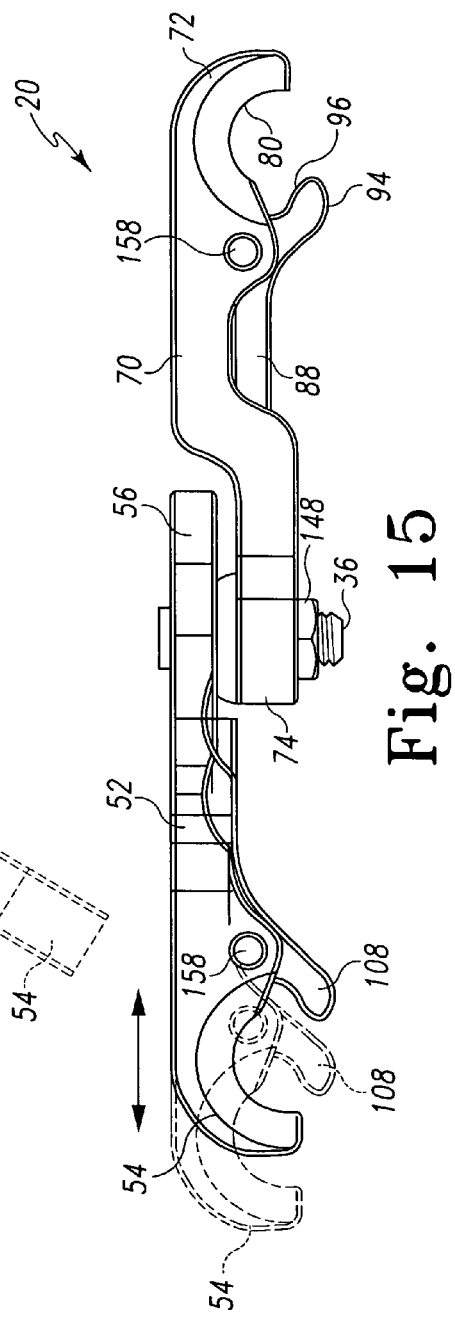

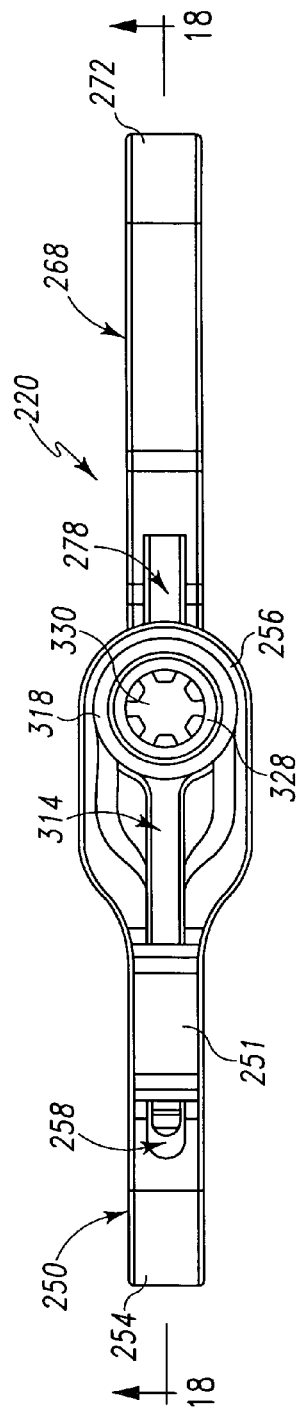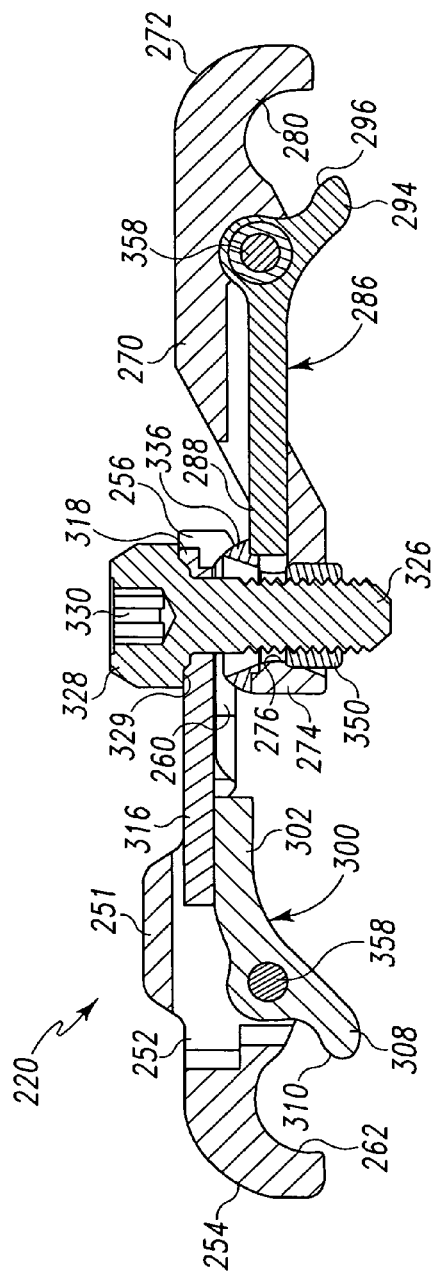

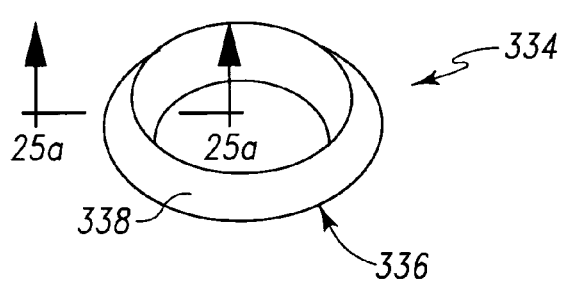
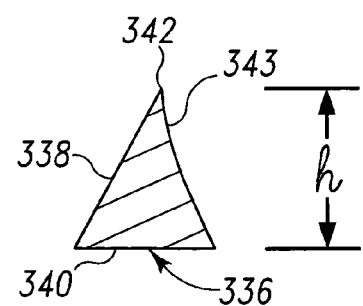
Fig. 25  Fig. 25A
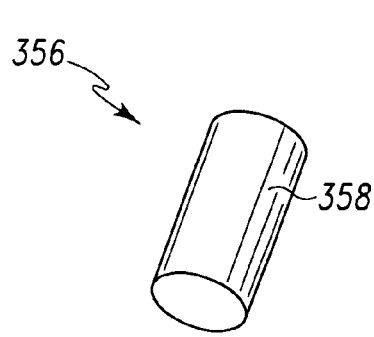
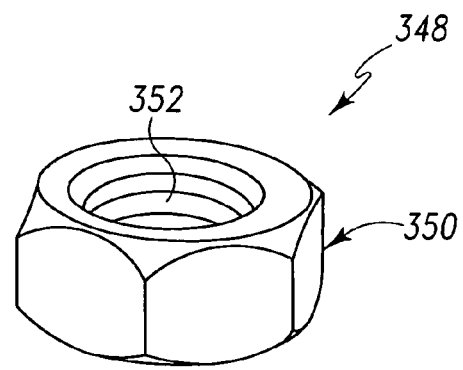
Fig. 26  Fig. 27

MULTI-AXIAL SPINAL CROSS-CONNECTORS

RELATED APPLICATIONS

This patent application claims the benefit of and/or priority to U.S. Provisional Patent Application Ser. No. 60/849,230 filed Oct. 4, 2006, entitled "Multi-Axial Spinal Cross-Connectors" the entire contents of which is specifically incorporated herein by reference.

BACKGROUND OF THE INVENTION

1. Field of the Invention

The present invention relates to spinal fixation devices and, in particular, to cross-connectors for connecting spinal fixation devices, such as spinal rods that are attached onto a patient's spine.

2. Background Information

There are many medical situations, because of disease, injury or deformity, where it is necessary to align and/or fix a desired relationship between adjacent vertebral bodies. In order to accomplish this goal, orthopedic spinal surgeons utilize spinal fixation devices to provide the desired relationship between adjacent vertebral bodies. Such spinal fixation devices typically include a spinal fixation element, such as a relatively rigid fixation rod, that is connected to adjacent vertebrae by attaching the rod to anchor devices implanted into the vertebrae.

Often, the spinal fixation rods are placed on opposite sides of the spinous process in a substantially parallel relationship. These spinal fixation rods may have pre-determined contours according to properties of the target implantation site. Once installed, the spinal fixation rods hold the vertebrae in a desired spatial relationship.

It may also be necessary in some circumstances to provide a spinal cross-connector at one or more points between the two spinal fixation rods in order to provide additional stability to the structure. Particularly, adjacent spinal fixation rod assemblies can be made more robust by using a cross-connector to bridge the pair of spinal rods.

While current spinal cross-connectors are effective, problems exist such as in mounting and maintaining the cross-connectors in a desired position and orientation with respect to the spinal rods. Other problems also exist with current cross-connectors such as sizing and locking issues.

Accordingly, there presently exists a need for an improved spinal cross-connector that can be easily installed and that securely mates and connects to spinal fixation devices such as spinal rods.

Accordingly, there also presently exists a need to provide an improved spinal rod connector that allows for both x-axis translation and x-axis rotation for coupling to adjacent spinal rods.

SUMMARY OF THE INVENTION

The present invention provides multi-axial spinal cross-connectors that are configured for connection between spinal fixation devices such as spinal fixation rods. The cross-connectors have first and second connection members that are joinable at a fixable pivot junction. The pivot junction allows the connection members to assume various positions relative to one another. A clamp is provided on each end of the first and second connection members whose open and closed states are controlled by fixation of the positions of the first and second connection members relative to each other.

The cross-connectors are formed of two links whose positions are adjustable relative to one another. The two links provide for rotation thereof in an X-X plane, and for linear translation thereof in an X-X axis. A central pivot is fixable to fix the positions of the links. Fixation structures for the central pivot allow the cross-connectors to be assembled, but unclamped so as to allow the cross-connectors to be situated onto adjacent spinal rods. Moreover, the fixation structures then allow the system to be clamped onto the spinal rods while still assembled.

The cross-connectors provide easily adjustable sizing between spinal rods. Moreover, the cross-connectors provide single and multi-step locking.

BRIEF DESCRIPTION OF THE DRAWINGS

The above mentioned and other features, advantages and objects of this invention, and the manner of attaining them, will become apparent and the invention itself will be better understood by reference to the following description of embodiments of the invention taken in conjunction with the accompanying drawings, wherein:

FIG. 2 is top view of the spinal rod cross connector of FIG. 1;

FIG. 3 is a sectional view of the spinal rod cross connector of FIG. 1 taken along line 3-3 of FIG. 2;

FIG. 14 is a top view of the spinal rod cross connector of FIG. 1 illustrating its x-axis rotation capabilities;

FIG. 15 is a side view of the spinal rod cross connector of FIG. 1 illustrating its x-axis translation capabilities;

FIG. 17 is top view of the spinal rod cross connector of FIG. 16;

FIG. 18 is a sectional view of the spinal rod cross connector of FIG. 16 taken along line 18-18 of FIG. 17;

FIG. 25 is a perspective view of a retaining ring of the spinal rod cross connector of FIG. 16;

FIG. 25a is a cross-sectional view of the retaining ring of FIG. 25 taken along line 25a-25a thereof;

FIG. 26 is a perspective view of a latch pin of the spinal rod cross connector of FIG. 16;

FIG. 27 is a perspective view of a retaining nut of the spinal rod cross connector of FIG. 16;

Like reference numerals indicate the same or similar parts throughout the several figures.

A detailed description of the features, functions and/or configuration of the components depicted in the various figures will now be presented. It should be appreciated that not all of the features of the components of the figures are necessarily described. Some of these non discussed features as well as discussed features are inherent from the figures. Other non discussed features may be inherent in component geometry and/or configuration.

DETAILED DESCRIPTION OF EMBODIMENTS OF THE INVENTION

Figure 1:
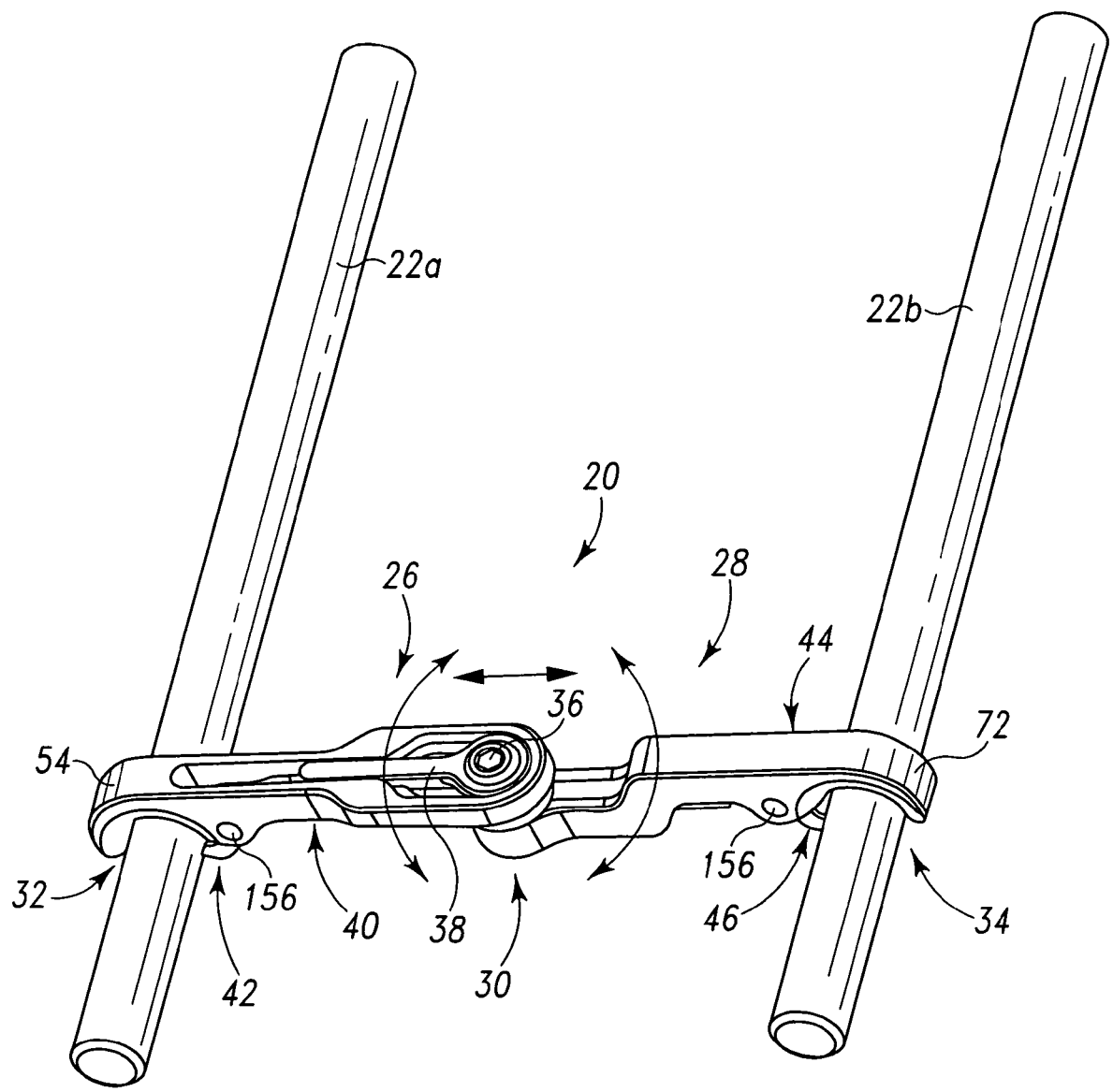
FIG. 1 a perspective view of an exemplary spinal rod cross connector fashioned in accordance with the present principles, the cross connector shown connected on both ends thereof to adjacent spinal rods.

Referring to FIGS. 1-15 and particularly to FIG. 1, there is depicted an exemplary embodiment of a spinal cross-connector generally designated 20 fashioned in accordance with the principles of the present invention shown coupled/connected onto and between two spinal rods 22a and 22b (spinal fixation elements). The spinal rods 22a and 22b are representative of any type of straight or contoured spinal rod, or they can represent other spinal elements or members of a spinal fixation system. The cross-connector 20 is generally made from a biocompatible material such as titanium. Other biocompatible materials or compounds may be used.

The cross-connector 20 has a first connection member 26 and a second connection member 28 attached to one another at a pivot junction 30. The first connection member 26 includes a first clamping structure 32 on one end thereof for clamping onto a spinal rod (shown in FIG. 1 as spinal rod 22a). The second connection member 28 includes a second clamping structure 34 on one end thereof for clamping onto a spinal rod (spinal rod 22b). The first and second connection members 26, 28 are adjustably joined about a set screw 36. As represented by the substantially horizontal linear arrow, the first and second connection members 26, 28 are movable (adjustable) relative to one another along their longitudinal axes (i.e. linear translation along the X-X axis). Also, as represented by the two double-headed arched arrows, the two connection members 26, 28 are movable about the pivot junction 30 about a plane of the X-X axis (i.e. rotational translation about the X-X axis). This is also discerned in FIG. 14.

Figure 4:
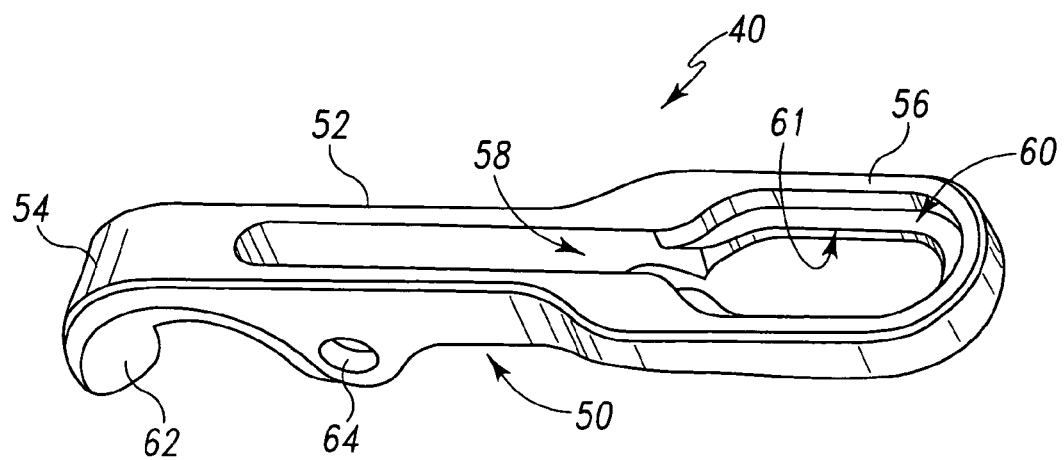
FIG. 4 is a perspective view of an upper hook of the spinal rod cross connector of FIG. 1.

The first connection member 26 includes a first connection arm 40 and a first latch member 42. As best seen in FIG. 4, the first connection arm 40 is defined by a body 50 fabricated from a suitable implantable material such as stainless steel, titanium, alloy, composite or the like. The body 50 has a neck 52 terminating at one end in a hook portion 54 and terminating at the other end in a head portion 56. The neck 52 includes an elongated slot 58 in communication with a cutout portion 60 of the head 56. The cutout portion 60 includes an inner groove 61. The hook portion 52 is configured with an inner surface or curvature 62 that is contoured to wrap around and abut a portion of a spinal rod. The neck 52 of the body 50 also includes a pivot bore 64 for receiving a pivot pin 156 (see e.g. FIG. 12) for pivotal coupling with the first latch member 42. FIG. 13 provides an enlarged view of the first connection arm 40. The first connection arm 40 provides a housing for the control arm 38. Particularly, the groove 61 of the first connection 40 receives and slidingly retains the annular head 118 of the control arm 38 (see FIG. 8).

Figure 7:
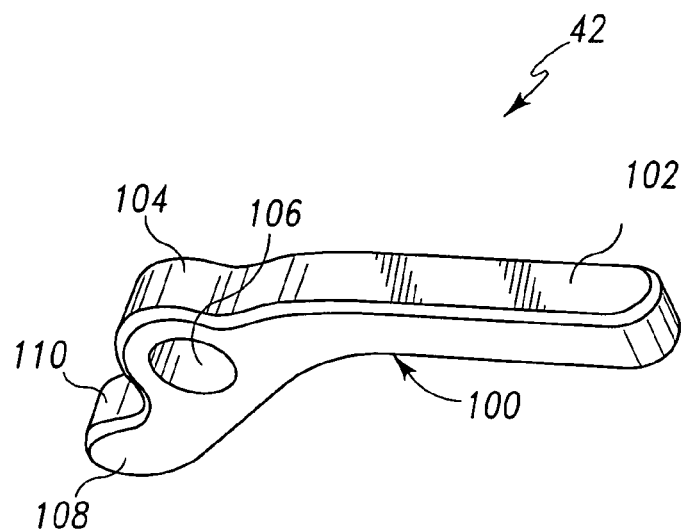
FIG. 7 is a perspective view of a short latch of the spinal rod cross connector of FIG. 1.

As best seen in FIG. 7, the first latch member 42 is defined by a body 101 fabricated from a suitable implantable material such as stainless steel, titanium, alloy, composite or the like. The body 100 defines a neck 102 having a generally rectangular cross section. A bore flange 104 is disposed proximate one end of the neck 102. The bore flange 104 carries a pivot bore 106. The body 100 also has a latch flange 108 that extends radially from a side of the bore flange 104. The latch flange 108 is configured to define an inner surface 110 that is contoured to wrap around and abut a portion of a spinal rod.

Figure 5:
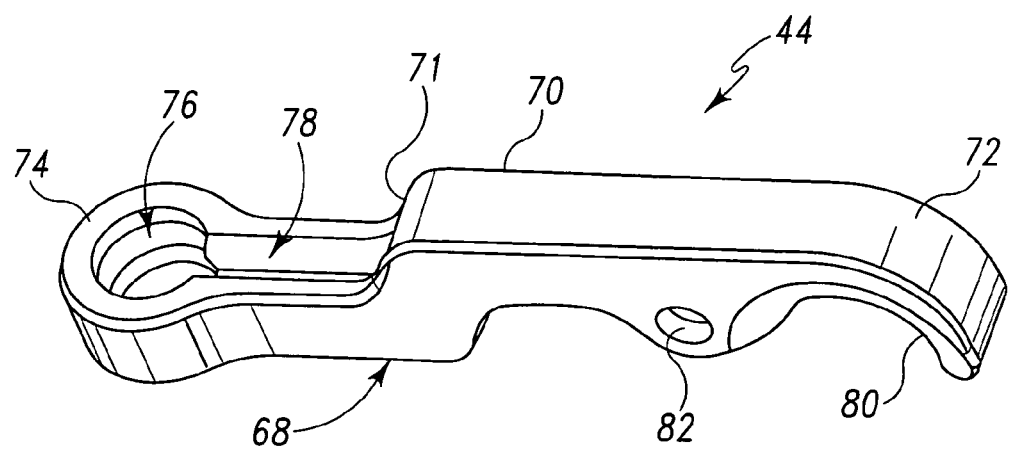
FIG. 5 is a perspective view of a lower hook of the spinal rod cross connector of FIG. 1.

The second connection member 28 includes a second connection arm 44 and a second latch member 46. As best seen in FIG. 5, the second connection arm 44 is defined by a body 68 fabricated from a suitable implantable material such as stainless steel, titanium, alloy, composite or the like. The body 68 has a neck 70 terminating at one end in a hook portion 72 and terminating at the other end in a head portion 74. The neck 70 includes a curved portion 71 between the hook portion 72 and the head portion 74. The neck also includes an elongated slot 78 in communication with a bore 76 of the head 74. The bore 76 is configured on its undersurface to partially receive the nut 148 and provide self tightening of the system. The hook portion 72 is configured with an inner surface or curvature 80 that is contoured to wrap around and abut a portion of a spinal rod. The neck 70 of the body 68 also includes a pivot bore 82 for receiving a pivot pin 156 (see e.g. FIG. 12) for pivotal coupling with the second latch member 46.

Figure 6:
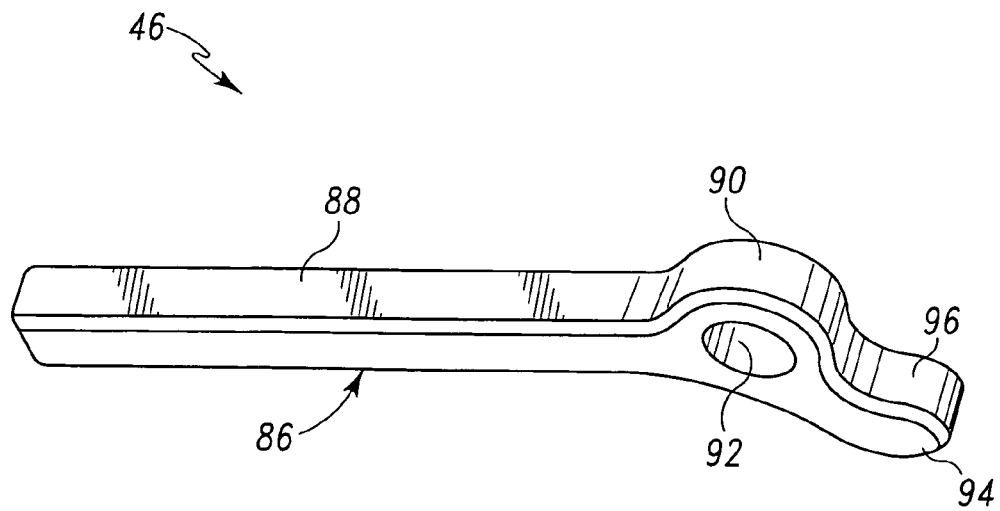
FIG. 6 is a perspective view of a long latch of the spinal rod cross connector of FIG. 1.

As best seen in FIG. 6, the second latch member 46 is defined by a body 86 fabricated from a suitable implantable material such as stainless steel, titanium, alloy, composite or the like. The body 86 defines a neck 88 having a generally rectangular cross section. A bore flange 90 is disposed proximate one end of the neck 88. The bore flange 90 carries a pivot bore 92. The body 86 also has a latch flange 94 that extends radially from a side of the bore flange 90. The latch flange 94 is configured to define an inner surface 96 that is contoured to wrap around and abut a portion of a spinal rod.

The first latch member 42 is pivotally connected to the first connection arm 40. The pivot bore 106 of the first latch member 42 is aligned with the pivot bore 64 of the first connection arm 40 and a pivot pin 156 is disposed therein. Likewise, the second latch member 46 is pivotally connected to the second connection arm 44. Therefore, the pivot bore 92 of the second latch member 46 is aligned with the pivot bore 82 of the second connection arm 44 and a pivot pin 156 is disposed therein.

Figure 12:
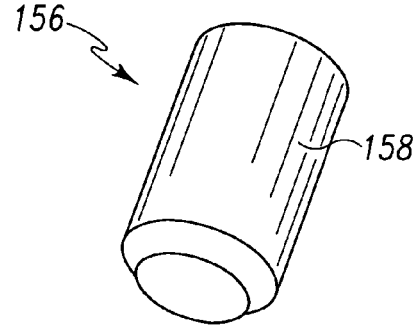
FIG. 12 is a perspective view of a latch pin of the spinal rod cross connector of FIG. 1.
Figure 13:
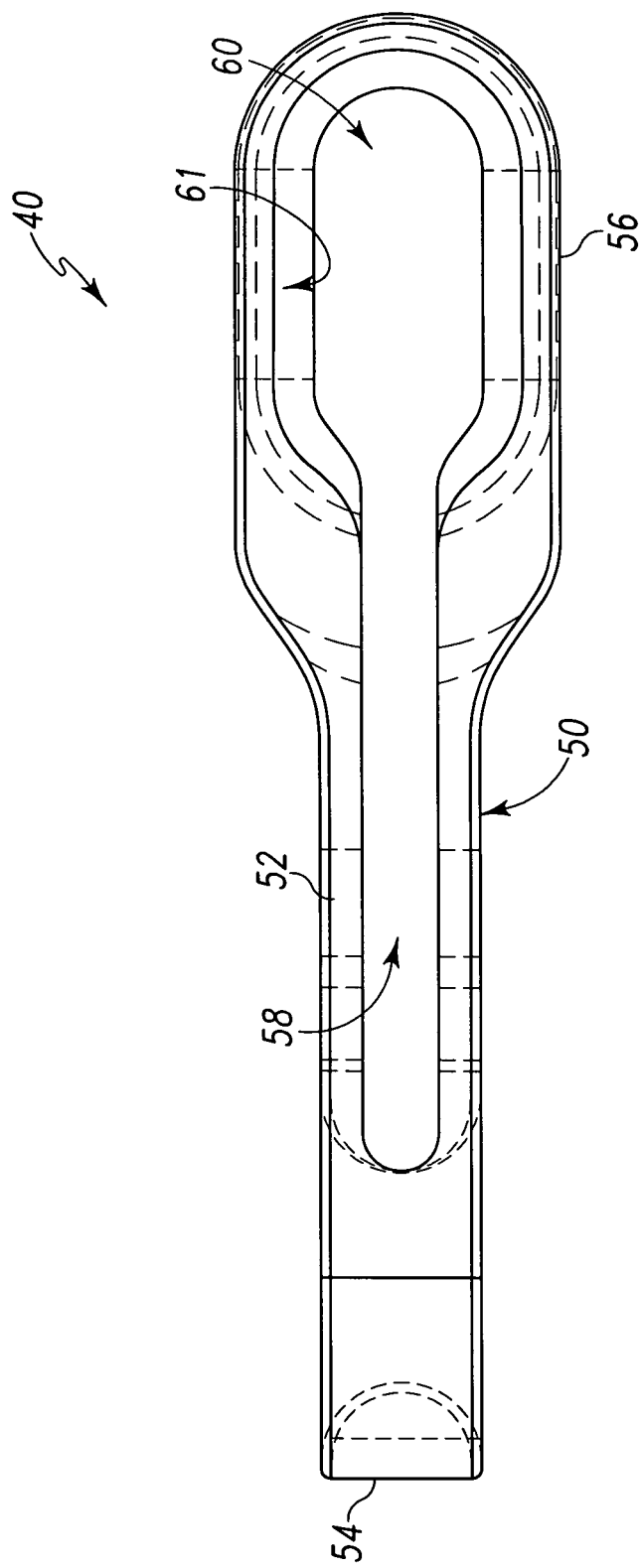
FIG. 13 is a top view of the upper hook.

FIG. 12 depicts an exemplary pivot pin 156. The pivot pin 156 is defined by a generally solid cylindrical body 158. The cylindrical body 158 is sized for reception in a particular pivot bore. The pivot pin 156 is fabricated from a suitable biocompatible material such as those described herein.

The first connection arm 40 and the second connection arm 44 are adjustably coupled to one another at the pivot junction 30. This is accomplished via a set screw 36, retaining ring 134 and retaining nut 148. Particularly, and as best seen in FIG. 3, the set screw 36 is received through the opening 60 of the first connection 40 and the bore 76 of the second connection arm 44. In this manner, the two connection arms are free to rotate about the set screw 36/pivot junction 30 (X-X rotation). The retaining ring 134 is situated between the heads 60, 74 of the first and second connection arms 40, 44. The retaining nut 148 is threadedly received onto the end of the set screw 36 to fix the position of the two connection arms relative to one another via compression.

Figure 9:
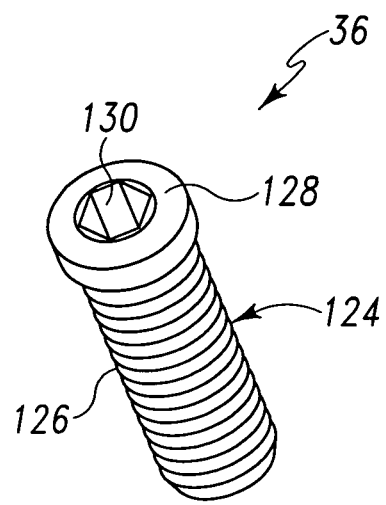
FIG. 9 is a perspective view of a set screw of the spinal rod cross connector of FIG. 1.

Referring briefly to FIG. 9, there is depicted an enlarged perspective view of the set screw 36. The set screw 36 is fabricated from a suitable bio-compatible material such as those described herein. The set screw 36 is defined by a body 124 having a threaded shank 126 and a head 128. A socket 130 is disposed in the head 128. The socket 130 is configured to allow a like-configured driver to be received therein and rotate the set screw 36.

Figure 10:
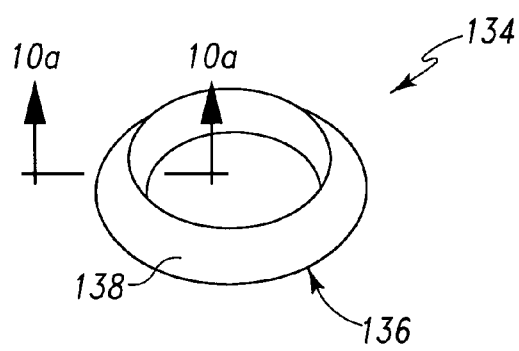
FIG. 10 is a perspective view of a retaining ring of the spinal rod cross connector of FIG. 1.
Figure 10A:
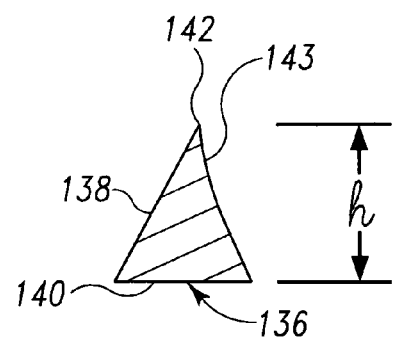
FIG. 10a is a cross-sectional view of the retaining ring of FIG. 10 taken along line 10a-10a thereof.

Referring briefly to FIGS. 10 and 10a, there is depicted an enlarged perspective view of the retaining ring 134. The retaining ring 134 is fabricated from a suitable bio-compatible material such as those described herein. The retaining ring 134 is defined by a body 136 formed of a generally triangular in cross-section band or ring 136. As best discerned in FIG. 10a, the band 136 defines a lower surface 140, an apex 142, an outer side 138 and an inner side 143. The band 136 also has a height of h. Moreover, the inner side 143 is slightly convex.

Figure 11:
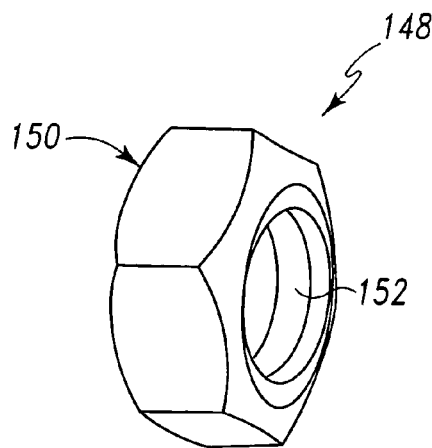
FIG. 11 is a perspective view of a retaining nut of the spinal rod cross connector of FIG. 1.

Referring briefly to FIG. 11, there is depicted an enlarged perspective view of the retaining nut 148. The retaining nut 148 is fabricated from a suitable bio-compatible material such as those described herein. The retaining nut 148 is defined by a generally hexagonal body 150. The body 150 has a threaded bore 152 therethrough.

As discerned in FIG. 13, the opening 60 of the head 56 is elongated to allow the set screw 36 to be adjustably positionable along its length. This permits longitudinal or X-X axis movement or translation of the set screw 36 relative to the first connection arm 40 (see, e.g. FIGS. 1-3). Since the set screw 36 is retained in the head and therefore fixed relative thereto, movement of the set screw 36 translates to movement of the second connection arm 44. Such translation is fixed upon tightening of the pivot junction 30. This permits the cross-connector 20 to assume a range of lengths to accommodate a range of spans between spinal rods. As shown in FIG. 14, the pivot junction 30 allows a change in orientation of one connection arm relative to the other connection arm. Again, such translation is fixed upon tightening of the pivot junction 30. This permits the cross-connector 20 to assume a range of angular orientations.

Referring back to FIGS. 1 and 3, the first latch member 42 cooperates with the first connection arm 40 to define the releasable clamping structure 32. Particularly, the hook portion 54 of the first connection arm 40 forms and/or defines an upper spinal rod reception area 62 to be received onto a spinal rod, while the latch flange 108 of the first latch member 42 defines a movable jaw to clamp onto the spinal rod particularly such that the spinal rod is received into the contour 110 of the latch flange 108. Pivoting of the first latch member 42 relative to the first connection arm 40 opens and closes the jaws (hook portion 54 and latch flange 108) of the clamp structure 32 to release and clamp the spinal rod 22a. Pivoting of the first latch member 42 thus controls the state of clamping. Therefore, control of pivoting controls clamping state. Once clamped, if pivoting is barred, the clamp will not be unclamped. This is controlled in clamp structure 32 by interface with the arm 102 of the body 100 of the first latch member 42.

Figure 8:
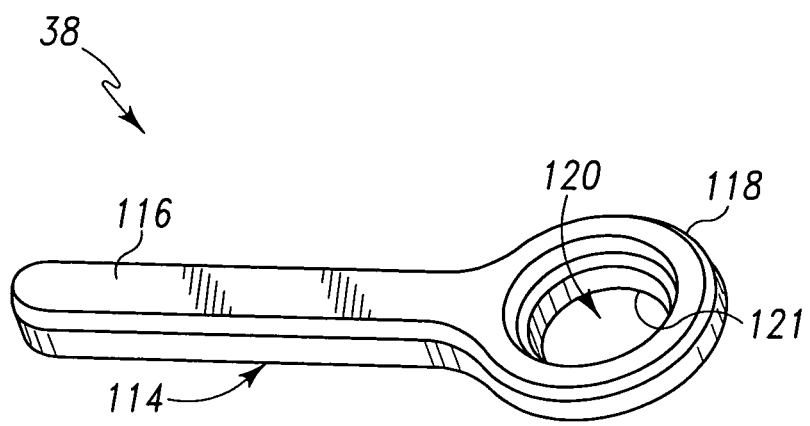
FIG. 8 is a perspective view of a slide (set) pin of the spinal rod cross connector of FIG. 1.

Particularly, pivoting of the first latch member 42 is controlled by a control arm 38. A control arm 38 is shown in FIG. 8. Briefly referring to FIG. 8, there is depicted an enlarged perspective view of the control arm 38. The control arm 38 is fabricated from a suitable bio-compatible material such as those described herein. The control arm 38 is defined by a body 114 having an arm 116 that extends from an annular portion or head 118. The head 118 has a bore 120 that is sized to receive the shank 126 of the set screw 36 but not the head 128 thereof. An interior annular ledge 121 is defined in the bore 120 that is sized to receive a portion of the head 128 in a "counter-sink" fashion.

The head 118 of the control arm 38 is received onto the set screw 36 such that movement of the set screw 36 moves the control arm 38. As such, the control arm 38 is free to rotate and linearly translate. Moreover, when installed, the arm 116 of the control arm 38 abuts the arm 102 of the first latch member 42 to block upward pivoting thereof (see, e.g. FIG. 3). This prevents unclamping of the clamp 32. When the arm 116 of the control arm 38 is not over the arm 102 of the first latch member 42, the first latch member 42 is free to pivot and thus unclamp the clamp 32.

The second latch member 46 cooperates with the second connection arm 44 to define the releasable clamping structure 34. Particularly, the hook portion 72 of the second connection arm 44 forms and/or defines an upper spinal rod reception area 80 to be received onto a spinal rod, while the latch flange 94 of the second latch member 46 defines a movable jaw to clamp onto the spinal rod particularly such that the spinal rod is received into the contour 96 of the latch flange 94. Pivoting of the second latch member 46 relative to the second connection arm 44 opens and closes the jaws (hook portion 72 and latch flange 94) of the clamp structure 34 to release and clamp the spinal rod 22b. Pivoting of the second latch member 46 thus controls the state of clamping. Therefore, control of pivoting controls clamping state. Once clamped, if pivoting is barred, the clamp will not be unclamped. This is controlled in clamp structure 34 by interface with the arm 88 of the body 86 of the second latch member 46.

Particularly, pivoting of the second latch member 46 is fixed by the retaining ring 136 (see, e.g. FIG. 3). When the set screw 36 is not tightened on the retaining ring 136, the arm 88 is not restrained and thus the second latch member 46 is free to pivot and thereby clamp and unclamp. The retaining ring 136 when placed on the set screw (an assembled state of the cross-connector 20) abuts the end of the arm 88 and thus restricts movement thereof. This also restricts pivoting of the second latch thereby fixing its clamped (typically the case) or unclamped position.

When assembled as depicted in the figures, the cross-connector is in a clamped position. Particularly, the clamps 32 and 34 are closed around the spinal rods 22a, 22b. Thus, fixing the position of the cross-connector fixes the clamping or puts the clamps in a clamped state.

Referring to FIG. 15, there is depicted the cross-connector 20 illustrating the longitudinal adjustability thereof particularly with respect to a clamp and clamp to clamp. As represented by the double-headed arrow, a connection arm may translate relative to the other connection arm which translates a clamp. In this manner, length of the cross-connector 20 to bridge the gap between the spinal rods 22a, 22b is adjustable.

Figure 16:
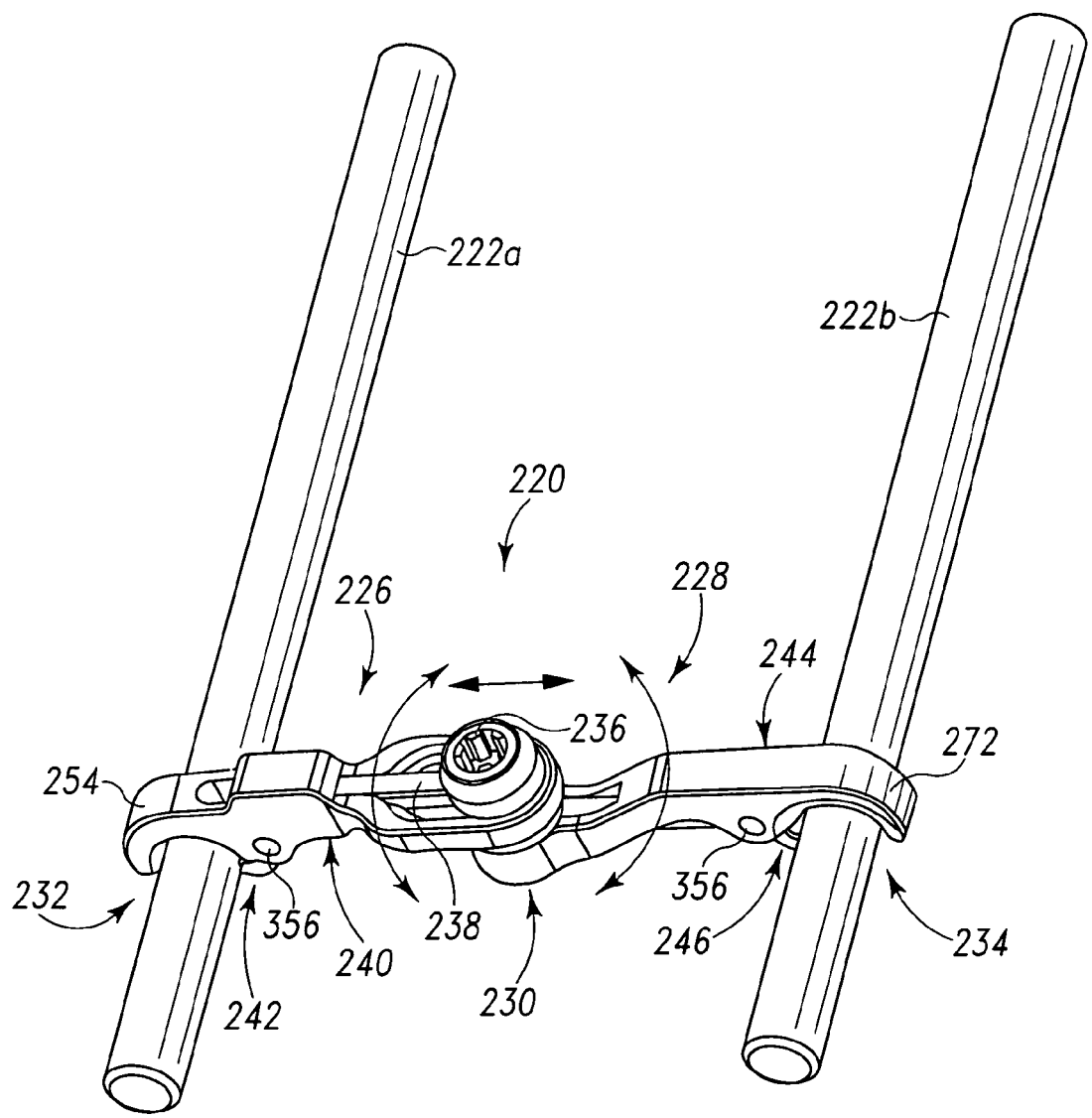
FIG. 16 a perspective view of another exemplary spinal rod cross connector fashioned in accordance with the present principles, the cross connector shown connected on both ends thereof to adjacent spinal rods.

Referring to FIGS. 16-29 and particularly to FIG. 16, there is depicted an exemplary embodiment of a spinal cross-connector generally designated 220 fashioned in accordance with the principles of the present invention shown coupled/connected onto and between two spinal rods 222a and 222b (spinal fixation elements). The spinal rods 222a and 222b are representative of any type of straight or contoured spinal rod, or they can represent other spinal elements or members of a spinal fixation system. The cross-connector 220 is generally made from a biocompatible material such as titanium. Other biocompatible materials or compounds may be used.

The cross-connector 220 has a first connection member 226 and a second connection member 228 attached to one another at a pivot junction 230. The first connection member 226 includes a first clamping structure 232 on one end thereof for clamping onto a spinal rod (shown in FIG. 16 as spinal rod 222a). The second connection member 228 includes a second clamping structure 234 on one end thereof for clamping onto a spinal rod (spinal rod 222b). The first and second connection members 226, 228 are adjustably joined about a set screw 236. As represented by the substantially horizontal linear arrow, the first and second connection members 226, 228 are movable (adjustable): relative to one another along their longitudinal axes (i.e. linear translation along the X-X axis). Also, as represented by the two double-headed arched arrows, the two connection members 226, 228 are movable about the pivot junction 230 about a plane of the X-X axis (i.e. rotational translation about the X-X axis).

Figure 19:
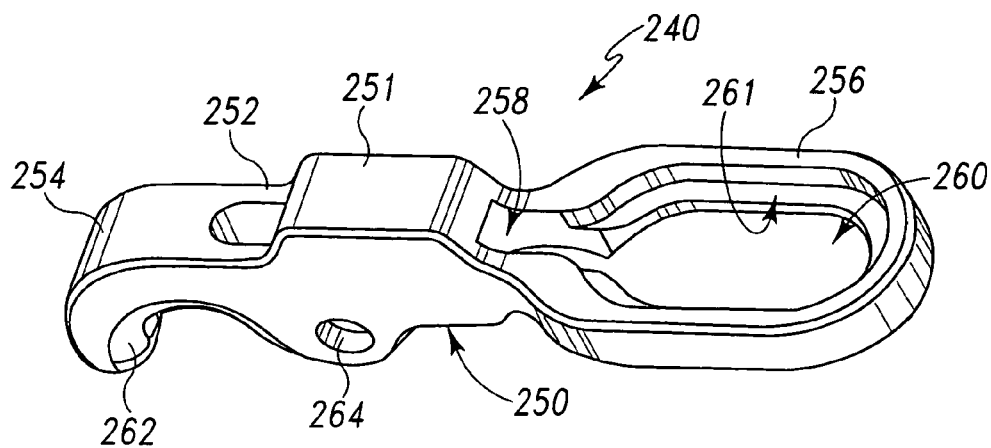
FIG. 19 is a perspective view of an upper hook of the spinal rod cross connector of FIG. 16.
Figure 28:
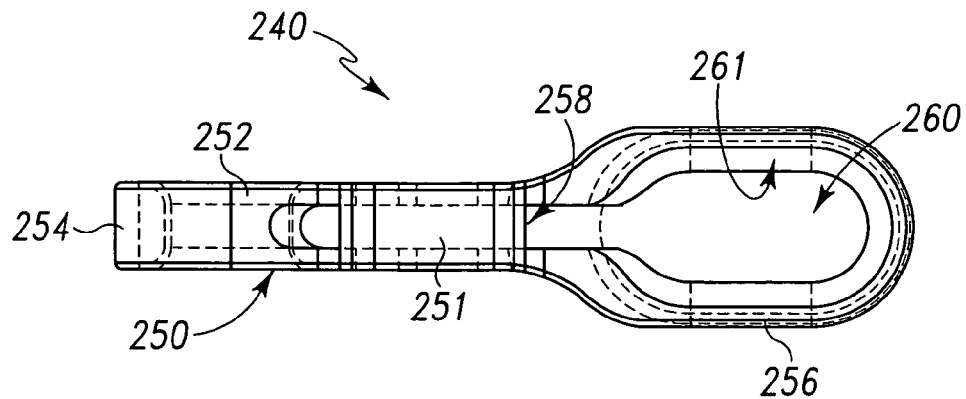
FIG. 28 is a top view of the upper hook.

The first connection member 226 includes a first connection arm 240 and a first latch member 242. As best seen in FIG. 19, the first connection arm 240 is defined by a body 250 fabricated from a suitable implantable material such as stainless steel, titanium, alloy, composite or the like. The body 250 has a neck 252 terminating at one end in a hook portion 254 and terminating at the other end in a head portion 256. The neck 252 includes an elongated slot 258 in communication with a cutout portion 260 of the head 256. The neck 252 also includes a cover 251 that extends over a portion of the slot 258. The cover 251 aids in retaining and guiding an arm 316 of the control arm 38 (see FIG. 23). The cutout portion 260 includes an inner groove 261. The hook portion 252 is configured with an inner surface or curvature 262 that is contoured to wrap around and abut a portion of a spinal rod. The neck 254 of the body 250 also includes a pivot bore 264 for receiving a pivot pin 356 (see e.g. FIG. 26) for pivotal coupling with the first latch member 242. FIG. 28 provides an enlarged top view of the first connection arm 240. The first connection arm 240 provides a housing for the control arm 238. Particularly, the groove 261 of the first connection 240 receives and slidingly retains the annular head 318 of the control arm 238 (see FIG. 23).

Figure 22:
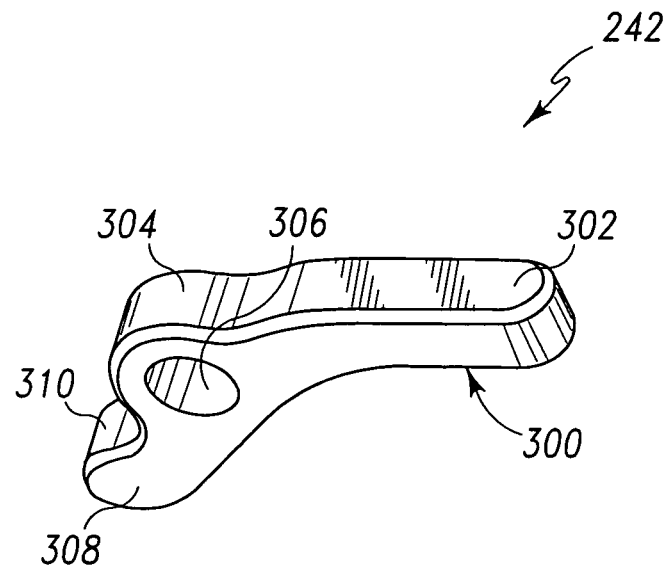
FIG. 22 is a perspective view of a short latch of the spinal rod cross connector of FIG. 16.

As best seen in FIG. 22, the first latch member 242 is defined by a body 300 fabricated from a suitable implantable material such as stainless steel, titanium, alloy, composite or the like. The body 300 defines a neck 302 having a generally rectangular cross section. A bore flange 304 is disposed proximate one end of the neck 302. The bore flange 304 carries a pivot bore 306. The body 300 also has a latch flange 308 that extends radially from a side of the bore flange 304. The latch flange 308 is configured to define an inner surface 310 that is contoured to wrap around and abut a portion of a spinal rod.

Figure 20:
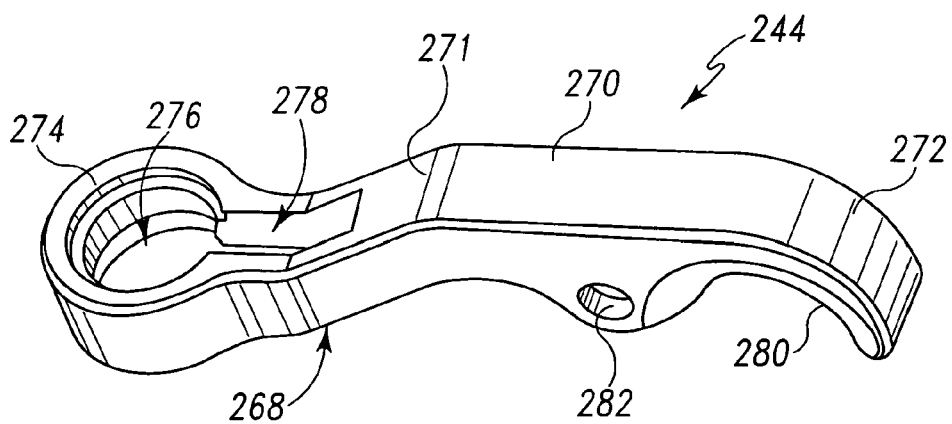
FIG. 20 is a perspective view of a lower hook of the spinal rod cross connector of FIG. 16.

The second connection member 228 includes a second connection arm 244 and a second latch member 246. As best seen in FIG. 20, the second connection arm 244 is defined by a body 268 fabricated from a suitable implantable material such as stainless steel, titanium, alloy, composite or the like. The body 268 has a neck 270 terminating at one end in a hook portion 272 and terminating at the other end in a head portion 274. The neck 270 includes a curved portion 271 between the hook portion 272 and the head portion 274. The neck also includes an elongated slot 278 emanating from a central opening 276 of the head 274. The opening 276 has a bore on one side that receives a counter-bore of the retaining ring 334, and a bore on its other side that receives the nut on a bottom side. The hook portion 272 is configured with an inner surface or curvature 280 that is contoured to wrap around and abut a portion of a spinal rod. The neck 270 of the body 268 also includes a pivot bore 282 for receiving a pivot pin 356 (see e.g. FIG. 26) for pivotal coupling with the second latch member 246.

Figure 21:
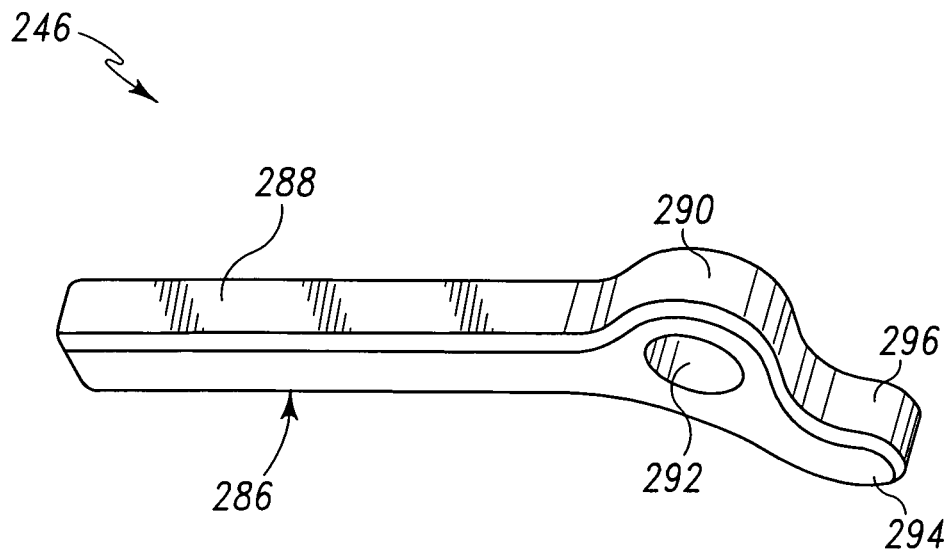
FIG. 21 is a perspective view of a long latch of the spinal rod cross connector of FIG. 16.

As best seen in FIG. 21, the second latch member 246 is defined by a body 286 fabricated from a suitable implantable material such as stainless steel, titanium, alloy, composite or the like. The body 286 defines a neck 288 having a generally rectangular cross section. A bore flange 290 is disposed proximate one end of the neck 288. The bore flange 290 carries a pivot bore 292. The body 286 also has a latch flange 294 that extends radially from a side of the bore flange 290. The latch flange 294 is configured to define an inner surface 296 that is contoured to wrap around and abut a portion of a spinal rod.

The first latch member 242 is pivotally connected to the first connection arm 240. The pivot bore 306 of the first latch member 242 is aligned with the pivot bore 264 of the first connection arm 240 and a pivot pin 356 is disposed therein. Likewise, the second latch member 246 is pivotally connected to the second connection arm 244. Therefore, the pivot bore 292 of the second latch member 246 is aligned with the pivot bore 282 of the second connection arm 244 and a pivot pin 356 is disposed therein.

FIG. 26 depicts an exemplary pivot pin 356. The pivot pin 356 is defined by a generally solid cylindrical body 358. The cylindrical body 358 is sized for reception in a particular pivot bore. The pivot pin 356 is fabricated from a suitable biocompatible material such as those described herein.

The first connection arm 240 and the second connection arm 244 are adjustably coupled to one another at the pivot junction 230. This is accomplished via a set screw 236, retaining ring 334 and retaining nut 348. Particularly, and as best seen in FIG. 18, the set screw 236 is received through the opening 260 of the first connection 240 and the bore 276 of the second connection arm 244. In this manner, the two connection arms are free to rotate about the set screw 236/pivot junction 230 (X-X rotation). The retaining ring 334 is situated between the heads 260, 274 of the first and second connection arms 240, 244. The retaining nut 348 is threadedly received onto the end of the set screw 236 to fix the position of the two connection arms relative to one another via compression.

Figure 24:
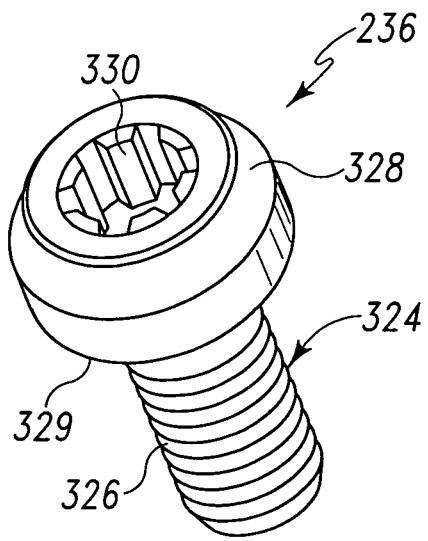
FIG. 24 is a perspective view of a set screw of the spinal rod cross connector of FIG. 16.

Referring briefly to FIG. 24, there is depicted an enlarged perspective view of the set screw 236. The set screw 236 is fabricated from a suitable bio-compatible material such as those described herein. The set screw 236 is defined by a body 324 having a threaded shank 326 and an oversized head 328. As such, the oversized head 328 defines an undersurface 329. As best seen in FIG. 18, the undersurface 329 of the head 328 overlies and abuts the head 318 of the control arm 238 and the ring 256 of the first connection arm 240. A socket 330 is disposed in the head 328. The socket 330 is configured to allow a like-configured driver to be received therein and rotate the set screw 236.

Referring briefly to FIGS. 25 and 25a, there is depicted an enlarged perspective view of the retaining ring 334. The retaining ring 334 is fabricated from a suitable bio-compatible material such as those described herein. The retaining ring 334 is defined by a body 336 formed of a generally triangular in cross-section band or ring 336. As best discerned in FIG. 25a, the band 336 defines a lower surface 340, an apex 342, an outer side 338 and an inner side 343. The band 336 also has a height of h. Moreover, the inner side 343 is slightly convex.

Referring briefly to FIG. 27, there is depicted an enlarged perspective view of the retaining nut 348. The retaining nut 348 is fabricated from a suitable bio-compatible material such as those described herein. The retaining nut 348 is defined by a generally hexagonal body 350. The body 350 has a threaded bore 352 therethrough.

As discerned in FIG. 28, the opening 260 of the head 256 is elongated to allow the set screw 236 to be adjustably positionable along its length. This permits longitudinal or X-X axis movement or translation of the set screw 236 relative to the first connection arm 240 (see, e.g. FIGS. 16-18). Since the set screw 236 is retained in the head and therefore fixed relative thereto, movement of the set screw 236 translates to movement of the second connection arm 244. Such translation is fixed upon tightening of the pivot junction 230. This permits the cross-connector 220 to assume a range of lengths to accommodate a range of spans between spinal rods. The pivot junction 230 allows a change in orientation of one connection arm relative to the other connection arm. Again, such translation is fixed upon tightening of the pivot junction 230. This permits the cross-connector 220 to assume a range of angular orientations.

Referring back to FIGS. 16 and 18, the first latch member 242 cooperates with the first connection arm 240 to define the releasable clamping structure 232. Particularly, the hook portion 254 of the first connection arm 240 forms and/or defines an upper spinal rod reception area 262 to be received onto a spinal rod, while the latch flange 308 of the first latch member 242 defines a movable jaw to clamp onto the spinal rod particularly such that the spinal rod is received into the contour 310 of the latch flange 308. Pivoting of the first latch member 242 relative to the first connection arm 240 opens and closes the jaws (hook portion 254 and latch flange 308) of the clamp structure 232 to release and clamp the spinal rod 222a. Pivoting of the first latch member 242 thus controls the state of clamping. Therefore, control of pivoting controls clamping state. Once clamped, if pivoting is barred, the clamp will not be unclamped. This is controlled in clamp structure 232 by interface with the arm 302 of the body 300 of the first latch member 242.

Figure 23:
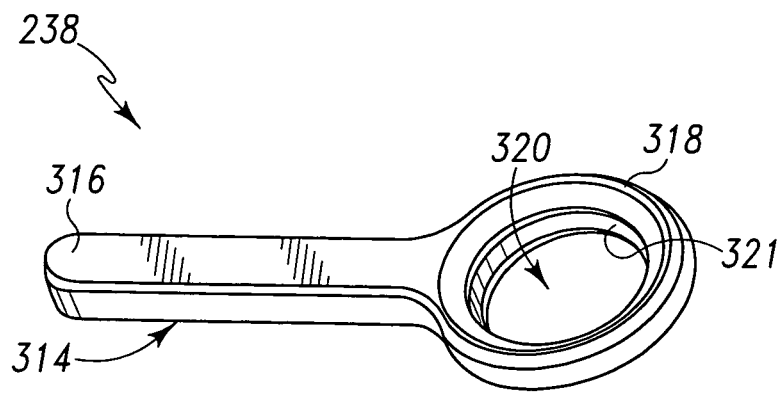
FIG. 23 is a perspective view of a slide (set) pin of the spinal rod cross connector of FIG. 16.

Particularly, pivoting of the first latch member 242 is controlled by a control arm 238. A control arm 238 is shown in FIG. 23. Briefly referring to FIG. 23, there is depicted an enlarged perspective view of the control arm 238. The control arm 238 is fabricated from a suitable bio-compatible material such as those described herein. The control arm 238 is defined by a body 314 having an arm 316 that extends from an annular portion or head 318. The head 318 has a bore 320 that is sized to receive the shank 326 of the set screw 236 but not the head 328 thereof. An interior annular ledge 321 is defined in the bore 320 that is sized to receive a portion of the head 328 in a "counter-sink" fashion.

The head 318 of the control arm 238 is received onto the set screw 236 such that movement of the set screw 236 moves the control arm 238. As such, the control arm 238 is free to rotate and linearly translate. Moreover, when installed, the arm 316 of the control arm 238 abuts the arm 302 of the first latch member 242 to block upward pivoting thereof (see, e.g. FIG. 18). This prevents unclamping of the clamp 232. When the arm 316 of the control arm 238 is not over the arm 302 of the first latch member 242, the first latch member 242 is free to pivot and thus unclamp the clamp 232. The housing of 240 abuts the control arm at the maximum height of the pivot to lock the latch arm 302.

The second latch member 246 cooperates with the second connection arm 244 to define the releasable clamping structure 234. Particularly, the hook portion 272 of the second connection arm 244 forms and/or defines an upper spinal rod reception area 280 to be received onto a spinal rod, while the latch flange 294 of the second latch member 246 defines a movable jaw to clamp onto the spinal rod particularly such that the spinal rod is received into the contour 296 of the latch flange 294. Pivoting of the second latch member 246 relative to the second connection arm 244 opens and closes the jaws (hook portion 272 and latch flange 294) of the clamp structure 234 to release and clamp the spinal rod 222b. Pivoting of the second latch member 246 thus controls the state of clamping. Therefore, control of pivoting controls clamping state. Once clamped, if pivoting is barred, the clamp will not be unclamped. This is controlled in clamp structure 234 by interface with the arm 288 of the body 286 of the second latch member 246.

Particularly, pivoting of the second latch member 246 is fixed by the retaining ring 336 (see, e.g. FIG. 18). When the retaining ring 336 is not placed on the set screw 236, the arm 288 is not restrained and thus the second latch member 246 is free to pivot and thereby clamp and unclamp. The retaining ring 336 when placed on the set screw (an assembled state of the cross-connector 220) abuts the end of the arm 288 and thus restricts movement thereof. This also restricts pivoting of the second latch thereby fixing its clamped (typically the case) or unclamped position.

When assembled as depicted in the figures, the cross-connector is in a clamped position. Particularly, the clamps 232 and 234 are closed around the spinal rods 222a, 222b. Thus, fixing the position of the cross-connector fixes the clamping or puts the clamps in a clamped state.

Figure 29:
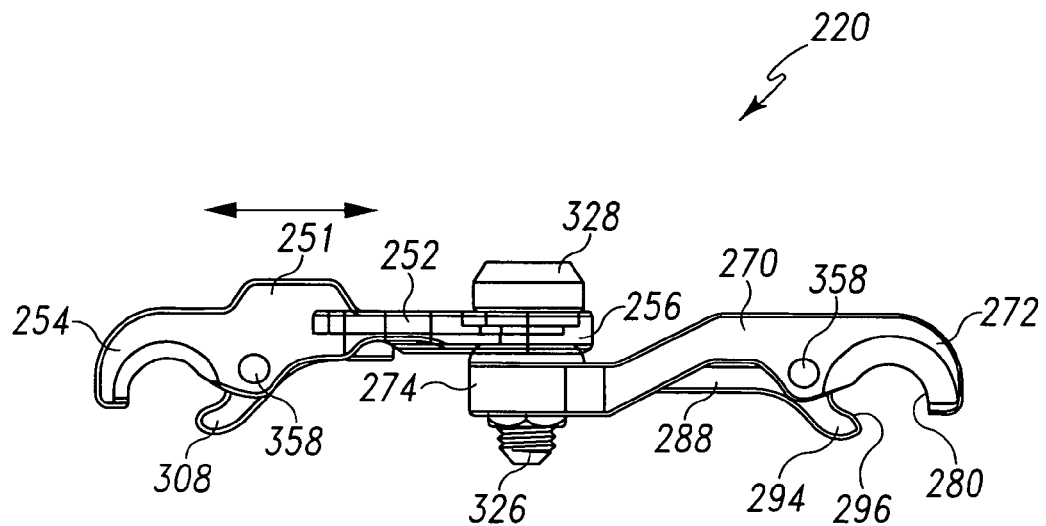
FIG. 29 is a side view of the spinal rod cross connector of FIG. 16 illustrating its x-axis translation capabilities.

Referring to FIG. 29, there is depicted the cross-connector 220 illustrating the longitudinal adjustability thereof particularly with respect to a clamp and clamp to clamp. As represented by the double-headed arrow, a connection arm may translate relative to the other connection arm which translates a clamp. In this manner, length of the cross-connector 220 to bridge the gap between the spinal rods 222a, 222b is adjustable.

While the invention has been illustrated and described in detail in the drawings and foregoing description, the same is to be considered as illustrative and not restrictive in character, it being understood that only preferred embodiments have been shown and described and that all changes and modifications that come within the spirit of the invention are desired to be protected.

What is claimed is:
1. A spinal cross connector comprising:
a first arm;
a first clamp structure on a first end of the first arm and configured to engage a first spinal rod;
a second arm; and
a second clamp structure on a first end of the second arm and configured to engage a second spinal rod;
the first and second arms connected to one another at second ends of the first and second arms via a pivot coupling configured to allow positioning of the first and second arms relative to one another and to fix positioning thereof, the pivot coupling having a pivot pin extending through overlapping openings in the second ends of the first and second arms, the pivot pin extending along a central axis which is perpendicular to a line extending from the first end of the first arm to the first end of the second arm, wherein position fixation of the first and second arms by the pivot coupling causes the first and second clamp structures to respectively engage the first and second spinal rods.

2. The spinal cross connector of claim 1, wherein:
the first clamp structure includes a first pivoting clamp member; and
the pivot coupling includes a fixation arm that interacts with the first pivoting clamp member to provide engagement of the first clamp structure to the first spinal rod upon position fixation of the first and second arms.

3. The spinal cross connector of claim 2, wherein the second clamp structure includes a second pivoting clamp member that interacts with the pivot coupling to provide engagement of the second clamp structure to the second spinal rod upon position fixation of the first and second arms.

4. The spinal cross connector of claim 3, wherein the first arm includes a channel and the fixation arm is disposed in the channel of the first arm.

5. The spinal cross connector of claim 2, wherein the pivot pin is threaded and provides position fixation through engagement with a threaded nut.

6. The spinal cross connector of claim 5, wherein the openings are located in first and second channels of the first and second arms respectively.

7. The spinal cross connector of claim 6, wherein the fixation arm is situated in the first channel.

8. The spinal cross connector of claim 7, wherein the first arm includes a retention member over the first channel that is configured to retain the fixation arm.

9. The spinal cross connector of claim 1, wherein:
wherein the first clamp structure includes a first pivoting latch member;
wherein the second clamp structure includes a second pivoting clamp member that interacts with the pivot coupling to provide engagement of the second clamp structure to the second spinal rod;
further comprising a control arm coupled to the pivot coupling and engaging the first latch member so that the first latch member engages the first spinal rod.

10. A spinal cross connector comprising:
a first arm;
a first clamp structure on a first end of the first arm and configured to engage a first spinal rod;
a second arm; and
a second clamp structure on a first end of the second arm and configured to engage a second spinal rod;
the first and second arms connected to one another at second ends of the first and second arms via a pivot coupling configured to allow positioning of the first and second arms relative to one another and to fix positioning thereof, wherein position fixation of the first and second arms by the pivot coupling causes the first and second clamp structures to respectively engage the first and second spinal rods
the first clamp structure includes a first pivoting clamp member; and
the pivot coupling includes a pivot pin that extends through overlapping openings in the second ends of the first and second arms, the pivot pin extending along a central axis which is perpendicular to a line extending from the first end of the first arm to the first end of the second arm, and a fixation arm that interacts with the first pivoting clamp member to provide engagement of the first clamp structure to the first spinal rod upon position fixation of the first and second arms;
wherein the second clamp structure includes a second pivoting clamp member that interacts with the pivot coupling to provide engagement of the second clamp structure to the second spinal rod upon position fixation of the first and second arms;
wherein the fixation arm is disposed in a first channel of the first arm.

11. A spinal cross connector comprising:
a first connector having a first end and a second end;
a first clamp associated with the first connector, the first clamp having a first spinal rod engagement position and a first spinal rod disengagement position;
a second connector having a first end and a second end; and
a second clamp associated with the second connector, the second clamp having a second spinal rod engagement position and a second spinal rod disengagement position;
the first and second connectors coupled via a pivot structure and configured to allow positioning of the first and second connectors relative to one another and to fix positioning thereof, the pivot structure having a threaded pivot pin extending through vertically aligned openings in the second ends of the first and second connectors, the pivot pin extending along a central axis which is perpendicular to a line extending from the first end of the first connector to the first end of the second connector, wherein position fixation of the first and second connectors by the pivot structure moves the first clamp from the first spinal rod disengagement position to the first spinal rod engagement position and the second clamp from the second spinal rod disengagement position to the second spinal rod engagement position.

12. The spinal cross connector of claim 1, wherein the first clamp includes a first pivoting clamp member; and
further comprising a fixation arm that interacts with the first clamp to move the first clamp into the first spinal rod engagement position.

13. The spinal cross connector of claim 12, wherein the second clamp includes a second pivoting clamp member that interacts with the pivot structure to move the second clamp into the second spinal rod engagement position.

14. The spinal cross connector of claim 13, wherein the pivot structure further includes a grommet that interacts with the second pivoting clamp member to move the second clamp into the second spinal rod engagement position.

15. The spinal cross connector of claim 14, wherein the fixation arm is disposed in a first channel of the first connector.

16. The spinal cross connector of claim 12, wherein the threaded pivot pin provides position fixation through engagement with a coupling connector.

17. The spinal cross connector of claim 16, wherein the openings are located in first and second channels of the first and second connectors respectively.

18. The spinal cross connector of claim 17, wherein the fixation arm is situated in the first channel.

19. The spinal cross connector of claim 18, wherein the first connector includes a retention member over the first channel that is configured to retain the fixation arm.

20. A spinal cross connector comprising:
a first arm having a first clamp structure on a first end thereof that is configured to engage a first spinal rod; and
a second arm having a second clamp structure on a first end thereof that is configured to engage a second spinal rod;
the first and second arms coupled to one another at second ends of the first and second arms via a coupling structure configured to allow linear and pivoting movement of the first and second arms relative to one another and to fix the positioning thereof, the pivot coupling having a threaded pivot pin extending through overlapping openings in the second ends of the first and second arms, wherein position fixation of the first and second arms by the coupling structure causes the first and second clamp structures to respectively engage the first and second spinal rods.

* * * * *